(12) United States Patent
Lindner et al.

(10) Patent No.: US 6,716,411 B2
(45) Date of Patent: Apr. 6, 2004

(54) METHOD FOR FINDING NUCLEOTIDE SYNTHESIS INHIBITORS HAVING FEWER SIDE EFFECTS

(75) Inventors: Jürgen Lindner, Marburg (DE); Burkhard Haase, Hofheim (DE)

(73) Assignee: Aventis Pharma Deustschland GmbH, Frankfurt am Main (DE)

(*) Notice: Subject to any disclaimer, the term of this patent is extended or adjusted under 35 U.S.C. 154(b) by 0 days.

(21) Appl. No.: 09/734,588

(22) Filed: Dec. 13, 2000

(65) Prior Publication Data

US 2002/0006381 A1 Jan. 17, 2002

(30) Foreign Application Priority Data

Dec. 15, 1999 (DE) .......................... 199 60 443

(51) Int. Cl.$^7$ .......................... A61K 49/00; A61K 31/42
(52) U.S. Cl. .......................... 424/9.1; 424/9.1; 424/9.2; 514/378; 514/326; 514/626
(58) Field of Search .................. 424/9.1, 9.2; 514/378, 514/326, 626

(56) References Cited

U.S. PATENT DOCUMENTS

| 4,965,276 A | * 10/1990 | Bartlett et al. ............... 514/378 |
| 5,728,721 A | 3/1998 | Bartlett ........................ 514/378 |
| 6,133,301 A | 10/2000 | Bartlett ........................ 514/378 |

FOREIGN PATENT DOCUMENTS

| DE | 41 27 737 | 2/1993 |
| WO | WO 97/34600 | 9/1997 |

OTHER PUBLICATIONS

Pharmacotherapy, A Pathophysiologic Approach, Elsevier, 1992, pp. 1890–1898.*
Goodman & Gilman's The Pharmacological Basis of Therapeutics, 1996, pp. 21–27, 46–55, 65–67, 1408.*
Wang A.X. et al.: "Synthesis and Immunosuppressant Activity of Pyrazole Carboxamides" Bioorganic & Medicinal Chemistry Letters, GB, Oxford, 8: 2787–2792 (1998).
Silva et al.: Pharmacokinetic/Pharmacodynamic (PK/PD): Strategy to Optimize Administration, Efficacy and Safety of the Malonitrilamides (MNA) A77 1726, HMR1279 and HMR1715 Journal of Heart and Lung Transplantation Abstract 148 (Jan. 1998).
Silva H.T. et al.: "Single–and–Multiple–Dose Pharmacokinetics and Pharmacodynamics of Leflunomide's Active Metabolite A77 1726 in Normal Lewis Rats" Transplantation Proceedings 28 (6): 3092–3094 (1996).
H. Burkhardt et al.; "Xenobiotic Immunosuppressive Agents: Therapeutic Effects In Animal Models of Autoimmune Diseases", Rheumatol Int. (1997) 17:85–90.
G. Kerby; "The Effect of Inflammation on the Level of Hexuronate–Containing Polysaccharides of Human Plasma", Arthritis and Rheumatism (1959) vol. II:44–45.
J. Taurog et al. "Adjuvant Arthritis", Methods in Enzymology (1988) vol. 162:339–355.
Translation of European Patent (UK) 0896537 Under Section 77 (6) (a).
H. Silva et al., "Leflunomide and Malononitrilamides" The American Journal of the Medical Sciences, vol. 313(5): 289–301 (1997).
Arthritis and Rheumatism: Official Journal of the American Rheumatism Association, vol. II, pp. 44–45 (1959).
Morgan, S.L., et al., "MTX Affects Inflammation and Tissue Destruction Differently in the Rat AA Model," The Journal of Rheumatology 28: 1476–1481 (2001).
Scheufler E., et al., "Pharmacokinetics and Organ Distribution of Methotrexate in the Rat[1]," Pharmacology 23:75–81 (1981).
Williams, J.W., et al., "Immunosuppressive Effects of Leflunomide in a Cardiac Allograft Model," Transplantation Proceedings, 25:745–746 (1993).
Mladenovic, V., et al., "Safety and Effectiveness of Leflunomide in the Treatment of Patients with Active Rheumatoid Arthritis," Arthritis & Rheumatism, 38:1595–1603 (1995).
J.K. Linder, et al., "Case Report: Curative Treatment of Pemphigus Vulgaris By Leflunomide," 4th International Conference on New Trends in Clinic and Experimental Immunosuppression, Program and Abstracts (2000).
Schorlemmer, H.U., et al., "Prolongation of Allogenic Transplanted Skin Grafts and Induction of Tolerance by Leflunomide, a–New Immunosuppressive," Transplantation Proceedings, 25:763–767 (1993).

* cited by examiner

Primary Examiner—Russell Travers
Assistant Examiner—Shahnam Sharareh
(74) Attorney, Agent, or Firm—Finnegan, Henderson, Farabow, Garrett, & Dunner, L.L.P.

(57) ABSTRACT

The invention relates to a method for finding nucleotide synthesis inhibitors which have a better therapeutic window. An efficacious dose of a nucleotide synthesis inhibitor is administered to a mammal. The concentration of the nucleotide synthesis inhibitor in the blood of the mammal is observed and it is determined whether the nucleotide synthesis inhibitor has a half-life which is shorter than that of N-(4-trifluoromethylphenyl)-2-cyano-3-hydroxycrotonamide. The invention also relates to a method of using nucleotide synthesis inhibitors in the treatment of immunological diseases.

5 Claims, No Drawings

METHOD FOR FINDING NUCLEOTIDE SYNTHESIS INHIBITORS HAVING FEWER SIDE EFFECTS

This application is a continuation of German application 19960443.6 filed on Dec. 15, 1999.

FIELD OF THE INVENTION

The present invention relates to a method for finding nucleotide synthesis inhibitors which have lower side effects and their use in treating immunological diseases.

BACKGROUND OF THE INVENTION

A fundamental problem of new medications is the relationship between tolerability and efficacy. The therapeutic window is the range between which an efficacious dose of a substance can be administered and a dose at which undesired side effects to a patient begin to occur. Generally, the larger the difference between the efficacious dose and the dose at which side effects begin to occur, the more harmless the administration of the substance and the more tolerable the substance is for the patient.

According to previous experience, cytostatic medications, including purine and pyrimidine synthesis inhibitors, have relatively narrow therapeutic windows. In addition, these medications induce side effects in a patient as a result of their main action; the suppression of the proliferation of cells. This property interferes more in the treatment of immunologically related diseases than in the treatment of oncological indications. Therefore, the use of cytostatic medications for the treatment of immunological diseases is restricted considerably.

Compounds which inhibit purine or pyrimidine synthesis are called nucleotide synthesis inhibitors (Burkhardt and Kalden; Rheumat. Int. (1997); 17: 85–90). These include, for example N-(4-trifluoromethylphenyl)-5methylisoxazole-4-carboxamide, N-(trifluoromethylphenyl)-2-cyano-3-hydroxycrotonamide, 2-cyano-3-cyclopropyl-3-hydroxyacrylic acid (4-cyanophenyl)amide or N-(trifluoromethylphenyl)-2-cyano-3-hydroxyhept-2-en-6-ynecarboxamide, brequinar(6-fluoro-2-(2'-fluoro[1,1'biphenyl]-4-yl)-3-methyl-4-quinolinecarboxylicacid), mycophenolate mofetil ((E)-6-(1, 3-dihydro-4-hydroxy-6-methoxy-7-methyl-3-oxoisobenzofuran-5-yl)--4-methyl-4-hexenoate), methotrexate (CAS No. 59-05-02), and mizoribine (CAS No. 50924-49-7).

Nucleotide synthesis inhibitors are beneficial to the treatment of immunologically related diseases such as rheumatoid arthritis or pemphigus vulgaris.

Disadvantages to the use of known nucleotide synthesis inhibitors include side effects such as problems relating to the gastrointestinal tract, bone marrow, and hair, etc. Slight side effects of these compounds are often only first discovered very late in the clinical development of a new medication. This sometimes leads to the discontinuation of development of these medications.

DETAILED DESCRIPTION OF THE INVENTION

This invention takes advantage of an observed reduction in side effects of nucleotide synthesis inhibitors in the treatment of immunological diseases. This reduction occurs when the nucleotide synthesis inhibitors only briefly reach the target in the body, which is sited intracellularly, and then, within a short time, fall to concentrations that no longer inhibit nucleotide biosynthesis. By means of this measure, it is possible in the treatment of immunological diseases to reduce the side effects of nucleotide synthesis inhibitors drastically without having to accept losses in the desired action on the immune system.

With this knowledge, it is possible within a short time to develop nucleotide synthesis inhibitors which exhibit a very good efficacy in the treatment of immunologically related diseases with a very low side effect rate.

The present invention relates to a method for finding nucleotide synthesis inhibitors which have lower side effects by determining the therapeutic window expected of cytostatic medications used in the treatment of immunological indications with the aid of a technically easily measurable property. This measurement can be used to determine the therapeutic window at even an early phase of development of these substances in pharmaceutical research.

The measurement is determined by calculating the half-life of a nucleotide synthesis inhibitor in the blood of a mammal, which is relevant for pharmacokinetic ratios in humans, or in humans in phase I clinical trial development, and comparing it with that of a known nucleotide synthesis inhibitor. The term "half-life" is understood as meaning the time in which the concentration of the nucleotide synthesis inhibitor in the blood plasma is halved. This invention for finding nucleotide synthesis inhibitors which have lower side effects therefore includes a) determining an efficacious dose of a nucleotide synthesis inhibitor in a mammal b) administering the nucleotide synthesis inhibitor in with efficacious dose to a mammal, c) determining the concentration of the nucleotide synthesis inhibitor in the blood of the mammal, and d) determining whether the nucleotide synthesis inhibitor has a half-life which is shorter than that of N-(-4-trifluoromethylphenyl)-2-cyano-3-hydroxycrotonamide.

Suitable mammals for carrying out pharmacokinetic comparison investigations include, but are not limited to, mice, rats, rabbits, dogs, monkeys or pigs. The half-life of the nucleotide synthesis inhibitor is preferably determined in humans. Depending on the animal and nucleotide synthesis inhibitor employed, the half-lives are very different. The half-life of N-(4-trifluoromethylphenyl)-2-cyano-3-hydroxycrotonamide is, for example, approximately 4 to 8 hours in rats and up to 350 hours in humans. Preferred nucleotide synthesis inhibitors are those which have a half-life of less than 150 hours, preferably less than 40 hours, in the blood plasma of humans.

The advantage of the present invention is that a statement of the expected therapeutic window of a nucleotide synthesis inhibitor being tested can be rapidly determined at a very early stage in pharmaceutical development via the measurement of the half-life in the blood plasma. Otherwise, the clinically utilizable dose range of a medicament is identified only by extensive clinical investigations with a therapy period of weeks or years. Therefore, a considerable acceleration in the development of the pharmaceutical is therefore possible.

The following examples illustrate that substances having a short half-life are preferable to substances having a long half-life in achieving the desired action of nucleotide synthesis inhibitors on the immune system with minimal side effects.

EXAMPLE 1

Dose-response relationship of N-(4-trifluoromethylphenyl)-2-cyano-3-hydroxycrotonamide The dose-response relationship of N-(4-trifluoromethylphenyl)-2-cyano-3-hyroxycrotonamide, hereafter referred to as compound 1, was drawn up in the adjuvant-induced arthritis model (method of Pearson C. M. and Wood F. D.; Arth. Rheum. 2: 44 (1959), and Taurog J. D., Argentieri D. C. et al., Meth. Enzymol. 162: 339 (1988)). The swelling of the paws, the formation of generalized symptoms of arthritis, know as the score index, the increase in the body weight during the experiment, and the survival of the animals were determined.

Compound 1 was administered orally from the start of the experiment onwards up to the end on day 21 in a 1% strength carboxymethlcellulose solution, (CMC). The control groups received corresponding amounts of 1% CMC without the active compound.

Six male Lewis rats having a body weight of approximately 210 g were employed in each experimental group.

Table 1 shows the results after day 21. Negative numbers indicate the worsening of the respective measurement parameter.

TABLE 1

| | Treatment group: | | | |
|---|---|---|---|---|
| | Reduction in paw swelling | Reduction in arthritis score | Increase in body weight | Surviving animals |
| Healthy control animals | — | — | 41% | 100% |
| Arthritis control | 0% | 0% | 12% | 100% |
| Experimental groups Compound 1 (mg/kg/day) | | | | |
| 1 | −9% | −11% | 10% | 100% |
| 2.5 | 78% | 70% | 20% | 100% |
| 5 | 96% | 83% | 37% | 100% |
| 7.5 | 105% | 87% | 25% | 100% |
| 10 | 96% | 84% | 11% | 100% |
| 15 | 106% | 91% | 8% | 100% |
| 25 | 114% | 96% | −2% | 100% |

In the adjuvant-induced arthritis model in the rat, autoimmune reactions are observed which correspond to the autoimmune diseases of the rheumatic type in humans.

Experiment 1 shows that compound 1 exhibited a very good therapeutic action in the rat even from a single daily dose of 2.5 mg/kg. Below a dose of 2.5 mg/kg, the action decreased drastically. At 1 mg/kg/day of compound 1, an action could no longer be determined.

EXAMPLE 2

Blood Plasma Level of Compound 1 in the Rat

A selective HPLC-MS/MS method was used for the detection of compound 1. The quantitative determination of compound 1 from the blood plasma was carried out as follows:

A solution of an internal standard, then 0.1 M NaOH solution and 1 ml of diethyl ether were added. The mixture was vigorously shaken and the organic phase was discarded. 0.5 N HCl solution was added to the aqueous phase, and the analyte and the internal standard were extracted with 1 ml of diethyl ether. The organic phase was evaporated and taken up in a 1:1 mixture of acetonitrile and water. 10 $\mu$l of this solution was injected into an HPLC unit.

The HPLC unit contained a Lichrospher C-18HD column. Using a flow rate of 1 ml/min, the analyte and the internal standard were eluted using the eluent combination acetonitrile+(ammonium acetate solution [10 mmolar]), 67+33, and then selectively detected by mass spectroscopy (LC-MS/MS analysis). During the analysis of the blood plasma samples, calibration samples were taken.

In order to test foreign substances in identical metabolic situations, compound 1 was given only to animals with adjuvant arthritis. The arthritis was induced according to Example 1. The animal weight was on average 210 g. Each group consisted of 6 male Lewis rats. Blood samples were obtained from the tail.

The influence on the blood plasma level of compound 1 was investigated by means of colestyramine. Compound 1 was employed in the lowest dose of 2.5 mg/kg/day, which still exhibits pharmacodynamic effects on adjuvant arthritis. During combination therapy with colestyramine, 1000 mg/kg of colestyramine was administered 4 hours after administration of the compound 1. Control animals received 1% CMC at the appropriate times without any active compound. The influence on the pharmacokinetics of compound 1 by colestyramine was investigated both after single administration and after chronic administration of compound 1 with or without colestyramine. Blood samples were obtained 2, 4, 6, 8, 24 and 48 hours after the last administration of compound 1.

Table 2a) shows pharmacokinetic parameters of compound 1 with and without colestyramine after a single administration; Table 2b) shows pharmacokinetic parameters of compound 1 with and without colestyramine after chronic administration:

TABLE 2 a)

| | 2.5 mg/kg of compound 1 | 2.5 mg/kg of compound 1 and 1000 mg/kg of colestyramine |
|---|---|---|
| Half-life (hours) | 3.85 | 3.32 |
| Area under the curve 0–48 hours ($\mu$g/ml × hr) | 141.69 | 99.90 |
| Maximum blood plasma level ($\mu$g/ml) | 10.15 | 9.62 |

The term "area under the curve" (AUC) is understood as meaning the area under the concentration level of a pharmaceutical substance plotted as a function of time. The AUC reflects the extent to which an organism is exposed to a substance. The term "chronic administration" is understood as meaning an administration of the compound 1 over a period of time which at least leads to constant blood levels of the compound 1. These constant blood levels, referred to as the steady state, are achieved after approximately 4 to 5 half-lives of regular taking.

TABLE 2 b)

| | 2.5 mg/kg of compound 1 | 2.5 mg/kg of compound 1 and 1000 mg/kg of colestyramine |
|---|---|---|
| Half-life (hours) | 3.45 | 3.47 |
| Area under the curve 0–48 hours ($\mu$g/ml × hr) | 63.58 | 37.81 |
| Maximum blood plasma level ($\mu$g/ml) | 5.73 | 4.66 |

It was observed that after administration of compound 1 identical peak blood levels were initially attained up to the time of 4 hours independently of whether cholestyramine was given after 4 hours or not. As a result of the administration of colestyramine, however, the blood levels of compound 1 were drastically reduced at later times.

It can be concluded from this experiment that by administration of colestyramine the blood levels of compound 1 can be markedly lowered after a previously undisturbed absorption phase. The AUC is reduced by 30% on single administration and by 40% on multiple administration.

EXAMPLE 3

Administration of Colestyramine to Reduce the Presence of Compound 1

Example 3 illustrates an experiment to determine whether the action of the minimally effective dose of compound 1 is reduced by administration of colestyramine at a time interval of 4 hours. This was investigated in the adjuvant-induced arthritis model. The model was carried out according to Example 1. Compound 1 was administered orally in 1% CMC daily from the start to the end of the investigation in a dose of 2.5 mg/kg/day. Colestyramine was likewise administered orally in 1% CMC 4 hours after the administration of compound 1. The corresponding control groups received equal volumes of a 1% CMC at the corresponding times. Table 3 shows the results:

TABLE 3

| | Treatment group: | | | |
|---|---|---|---|---|
| | Reduction in paw swelling | Reduction in arthritis score | Increase in body weight | Surviving animals |
| Healthy control animals | — | — | 30% | 100% |
| Arthritis control | 0% | 0% | 17% | 100% |
| 1000 mg/kg/day of cholestyramine | −14% | −3% | 22% | 100% |
| 2.5 mg/kg/day of compound 1 | 78% | 70% | 20% | 100% |
| 2.5 mg/kg/day of compound 1 and 1000 mg/kg/day of cholestyramine | 86% | 81% | 20% | 100% |

In Example 3, we investigated whether relatively constant blood levels existing over a fairly long time were responsible for the desired effects of compound 1 on the immune system, or whether blood levels occurring for a short time (peak blood levels) of compound 1 caused this effect.

For this, compound 1 was administered orally once daily at the lowest efficacious dose of 2.5 mg/kg/day (see Example 1). In the corresponding comparison groups, colestyramine was administered 4 hours after administration of compound 1 in order to lower the blood levels of compound 1 in an accelerated manner after the absorption phase had taken place. By means of this, the action of blood levels of compound 1 existing for different lengths of time on the immunologically related pathological processes in adjuvant-induced arthritis in the rat was investigated. No difference was seen in the desired action of compound 1 on adjuvant-induced arthritis independently of whether colestyramine was given 4 hours after the administration of compound 1 or not.

Since, at the lowest efficacious dose of compound 1, the reduction in the blood levels from 4 hours after administration led to no reduction in the action of compound 1, it was concluded that only the peak blood levels were responsible for the action and not persistent blood levels of the compound 1.

Using Examples 2 and 3, the observations from the clinic on humans (see Example 4) were confirmed. For the action of N-(4-trifluoromethylphenyl)-5-methylisoxazole-4-carboxamide (leflunomide), only short-term peak blood levels were needed and persistent blood levels did not contribute to the efficacy of leflunomide.

EXAMPLE 4

Observation of Leflunomide Treatment in Humans

In one patient who was suffering from the immunologically related disease, pemphigus vulgaris, the symptoms of this autoimmune disease completely disappeared under therapy with N-(4-trifluoromethylphenyl)-5-methylisoxazole-4-carboxamide (leflunomide). However, the patient suffered from permanent diarrhea as a result of this treatment. This diarrhea adversely affected the quality of life of the patient. Because of the problems caused by this side effect, an attempt was made, after more than two years' therapy with a constant dose of 20 mg of leflunomide per day, to end the therapy. Four days following the discontinuation of the leflunomide, it was observed that the autoimmune disease pemphigus vulgaris occurred again severely. The side effects of the leflunomide therapy, however, did not disappear within this period.

This observation was surprising, as the active metabolite of leflunomide, compound 1, has a half-life of approximately 14 days in humans. Furthermore, in this patient the blood levels of the active metabolite of leflunomide were repeatedly determined in the relatively high range between 70 mg/l and 85 mg/l. Investigations on patients who suffer from rheumatoid arthritis and had been treated with leflunomide showed blood levels of over 32 mg/l of the compound 1.

From these observations, it was concluded that the relatively slowly decreasing blood level of compound 1 present in this patient was indeed responsible for the side effects, but not for the desired action on the immune system.

Furthermore, these observations showed that the desired actions of leflunomide on the immune system were caused by the short-term relatively low local peak concentration of leflunomide and/or of the compound 1 after absorption and not by the high constant blood levels of the compound 1.

It is evident from these observations that a highly tolerable nucleotide synthesis inhibitor should reach its site of action only briefly in order to exert its desired effects on the immune system there without leading to considerable side effects. Surprisingly, remaining at the site of action longer does not contribute to an increase in the activity on the immune system, but only to an increase in the undesired side effects.

This effect can be achieved using substances which, like leflunomide and/or compound 1, are inhibitors of nucleotide biosynthesis, but have a shorter residence time at the site of action (half-life) in the body.

EXAMPLE 5

The Tolerability of Constant Blood Levels of the Compound 1 Compared to Blood Levels of the Compound 1 Occurring in a Pulse-like Manner Example 5 shows the tolerability of constant blood levels of compound 1 compared to blood levels of compound 1 occurring in a pulse-like manner. In order to attain constant blood levels, a mini-infusion pump was subcutaneously implanted into experimental animals. The mini-infusion pumps contained 2 ml of a 15% strength ethanolic solution of compound 1, which was continuously released over 28 days. Doses of 2.5, 5, 10 and 25 mg/kg/day were employed. For comparison, animals which received the same daily doses of the compound 1, but administered orally, were implanted with mini-infusion pumps; these, however, were filled with only the vehicle (15% ethanol in water). A 1% strength CMC was additionally administered orally to animals which received the compound 1 via mini-infusion pumps. The survival of the animals was taken as a course parameter. Additionally, blood was taken on day 5 and day 27 in order to determine the blood levels of compound 1. Blood was taken from animals 4 hours after oral administration of compound 1. The group was comprised of 6 male Lewis rats having a body weight of approximately 210 g. Corresponding to the preceding experiments, adjuvant arthritis was induced in the animals on day 5. Table 4 shows the results:

Observation of lefunomide treatment in humans

TABLE 4

| | Treatment group: | | | |
|---|---|---|---|---|
| | Compound 1 blood plasma level (day 5) | Compound 1 blood plasma level (day 27) | Body weight increase | Surviving animals |
| Healthy animals Control group | — | — | 36% | 100% |
| Arthritis control | — | — | -4% | 100% |
| 2.5 mg/kg/day of compound 1 p.o. | not determined | 9.66 µg/ml ± 1.56 | +29% | 100% |
| 5 mg/kg/day of compound 1 p.o | 14.31 µg/ml ± 2.85 | 18.0 µg/ml ± 3.76 | +25% | 100% |
| 10 mg/kg/day of compound 1 p.o. | not determined | 34.35 µg/ml ± 4.98 | +27% | 100% |
| 25 mg/kg/day of compound 1 p.o. | not determined | 80.5 µg/ml ± 6.53 | -2% | 100% |
| 2.5 mg/kg/day of compound 1 - mini-infusion - | 2.05 µg/ml ± 0.48 | 2.34 µg/ml ± 0.58 | +22% | 100% |
| 5 mg/kg/day of compound 1 - mini-infusion - | 3.57 µg/ml ± 1.50 | 4.18 µg/ml ± 0.84 | +26% | 100% |
| 10 mg/kg/day of compound 1 - mini-infusion - | 4.55 µg/ml ± 2.92 | 6.72 µg/ml ± 1.10 | +29% | 100% |
| 25 mg/kg/day of compound 1 - mini-infusion - | not determined animals too weak | not determined animals too weak | +13%* | 17% |

*in this group only 1 of 6 animals survived, the body weight increase was therefore only determined in one animal; p.o. means orally.

Example 5 shows that constant blood levels of the compound 1 are less tolerable than high blood levels occurring short-term.

For the attainment of constant blood levels of compound 1, the animals were implanted subcutaneously with a mini-infusion pump which supplied compound 1 to the animals continuously for 28 days. By means of this pump, constant blood levels of compound 1 were attained. Thus long half-lives of compound 1, such as are observed in humans, were simulated.

For the comparison group, animals were treated with the identical daily dose of compound 1, but received the substance orally rather than by mini-infusion pump. Orally administered compound 1 exhibits a short half-life of approximately 4 to 8 hours in the rat, as determined in Example 2.

In this experiment, the tolerability of the compound 1 with a short half-life (compound 1 orally administered) was compared with the tolerability of the compound 1 with a long half-life (compound 1 by pump with a constant infinite half-life). The doses employed were 2.5 mg/kg/day, 5 mg/kg/day, 10 mg/kg/day and 25 mg/kg/day. The number of animals surviving the treatment was used as a measure of the tolerability. The tolerability was moreover compared with respect to the observed blood levels.

Ninety three percent of the animals which received 25 mg/kg/day of compound 1 with the mini-infusion pump died. In contrast to this, all animals to which the 25 mg/kg/day dose was orally administered survived. This experiment shows that constant blood levels of the compound 1 with the same daily substance load were substantially more poorly tolerated than blood levels of the compound 1 occurring briefly and decreasing again.

The blood levels of the animals with mini-infusion pumps were approximately identical on day 5 after the start of the experiment and at the end of the experiment. Depending on the dose set, the animals with an infusion pump showed blood plasma values of the compound 1 of 2.34 µg/ml, 4.18 µg/ml and 6.72 µg/ml. Because of the poor condition of the animals in the 25 mg/kg dose group, no blood could be taken from the animals.

From the values at lower doses, however, it was extrapolated that in the 25 mg/kg/day dose group, which received compound 1 via a mini-infusion pump, the blood plasma levels could not have been above 15 µg/ml. The animals under oral administration of compound 1 showed significantly higher blood plasma values of 9.66 µg/ml, 18.01 µg/ml, 34.35 µg/ml and 80.50 µg/ml.

The comparison of the blood levels thus shows that animals under oral administration of the compound 1 had significantly higher blood levels (approximately 4 to 5 times higher) than animals with the mini-infusion pump.

Example 5 therefore shows that constant blood levels of compound 1 were substantially more poorly tolerated than blood levels occurring in a pulse-like fashion, even if these were 4 to 5 times higher than the constant blood levels. This result is in agreement with the original clinical observation that the constant blood levels of compound 1 observed in humans were responsible for its side effects.

Example 5 shows that substances which have the activity of the compound 1 but exhibit shorter half-lives were substantially better tolerated than substances having a long half-life.

We claim:

1. A method for determining the therapeutic window of a purine or pyrimidine nucleotide synthesis inhibitor in inhibiting purine or pyrimidine nucleotide biosynthesis comprising the steps of:
   a) determining an efficacious dose of said nucleotide synthesis inhibitor in a mammal;
   b) administering said nucleotide synthesis inhibitor in said efficacious dose to said mammal;
   c) determining the concentration of said nucleotide synthesis inhibitor in the blood of said mammal; and
   d) determining whether said nucleotide synthesis inhibitor has a half-life which is shorter than that of N-(4-trifluoromethylphenyl)-2-cyano-3-hydroxycrotonamide wherein said shorter half-life is an indication of a wider therapeutic window of said purine or pyrimidine nucleotide synthesis inhibitor than N-(4-trifluoromethylphenyl)-2-3-hydroxycrotonamide in inhibiting purine or pyrimidine nucleotide biosynthesis.

2. The method as recited in claim 1, wherein said mammal comprises a mouse, rat, rabbit, dog, monkey, or pig.

3. The method recited in claim 1, wherein said mammal is a human.

4. The method as recited in claim 3, wherein the half-life of said nucleotide synthesis inhibitor in the blood plasma of said human is less than 150 hours.

5. The method as recited in claim 4 wherein said half life of said nucleotide synthesis inhibitor is less than 40 hours.

* * * * *